United States Patent
Li

(10) Patent No.: US 9,708,907 B2
(45) Date of Patent: Jul. 18, 2017

(54) APPARATUS AND METHOD FOR ESTIMATING FORMATION LITHOLOGY USING X-RAY FLOURESCENCE

(75) Inventor: Fusheng Li, Houston, TX (US)

(73) Assignee: BAKER HUGHES INCORPORATED, Houston, TX (US)

( * ) Notice: Subject to any disclaimer, the term of this patent is extended or adjusted under 35 U.S.C. 154(b) by 1222 days.

(21) Appl. No.: 13/409,289

(22) Filed: Mar. 1, 2012

(65) Prior Publication Data

US 2013/0066605 A1   Mar. 14, 2013

Related U.S. Application Data

(60) Provisional application No. 61/479,213, filed on Apr. 26, 2011.

(51) Int. Cl.
*G01N 23/223* (2006.01)
*E21B 49/06* (2006.01)
*E21B 49/10* (2006.01)
*G01N 33/24* (2006.01)

(52) U.S. Cl.
CPC .............. *E21B 49/06* (2013.01); *E21B 49/10* (2013.01); *G01N 23/223* (2013.01); *G01N 33/241* (2013.01); *G01N 2223/076* (2013.01)

(58) Field of Classification Search
USPC .................. 702/8, 9, 11, 28, 30, 75, 76, 172
See application file for complete search history.

(56) References Cited

U.S. PATENT DOCUMENTS

| | | |
|---|---|---|
| 3,063,922 A | 6/1976 | Zulliger, at al. |
| 4,016,419 A | 4/1977 | Kotani et al. |
| 4,045,676 A | 8/1977 | Rolle |
| 4,417,355 A | 11/1983 | Anisovich et al. |
| 4,492,863 A | 1/1985 | Smith, Jr. |
| 4,510,573 A | 4/1985 | Boyce et al. |
| 4,722,095 A | 1/1988 | Muegge et al. |
| 4,996,421 A | 2/1991 | Rai et al. |
| 5,105,894 A | 4/1992 | Enderlin |

(Continued)

FOREIGN PATENT DOCUMENTS

| | | |
|---|---|---|
| EP | 1357401 | 10/2003 |
| WO | 2010055392 A2 | 5/2010 |

OTHER PUBLICATIONS

Notification of Transmittal of the International Search Report and the Written Opinion of the International Searching Authority, or the Declaration; PCT/US2012/034969; Nov. 1, 2012.

(Continued)

*Primary Examiner* — Mohamed Charioui
(74) *Attorney, Agent, or Firm* — Cantor Colburn LLP

(57) ABSTRACT

An apparatus for estimating properties of an earth formation includes a carrier configured to be disposed in a borehole in the earth formation, and a sample retriever configured to remove a sample of the earth formation, the sample including solid components of the earth formation. The apparatus also includes an analysis assembly including a chamber disposed with the carrier and configured to hold the sample, an X-ray source configured to irradiate the sample with X-ray radiation while the sample is disposed in the chamber, and one or more X-ray detectors configured to detect radiation emitted from the sample in response to irradiation from the X-ray source.

20 Claims, 7 Drawing Sheets

(56) References Cited

U.S. PATENT DOCUMENTS

| | | | |
|---|---|---|---|
| 5,668,373 A * | 9/1997 | Robbat et al. | 250/339.12 |
| 6,023,496 A | 2/2000 | Kuwabara | |
| 6,041,095 A | 3/2000 | Yokhin | |
| 6,097,785 A * | 8/2000 | Elam | 378/45 |
| 6,130,931 A | 10/2000 | Laurila et al. | |
| 6,254,272 B1 | 7/2001 | Dilick | |
| 6,345,086 B1 | 2/2002 | Ferrandino et al. | |
| 6,507,401 B1 * | 1/2003 | Turner et al. | 356/436 |
| 6,588,266 B2 | 7/2003 | Tubel et al. | |
| 7,201,221 B2 | 4/2007 | Tubel et al. | |
| 7,507,952 B2 | 3/2009 | Groves et al. | |
| 7,542,543 B2 | 6/2009 | Shampine et al. | |
| 7,614,294 B2 | 11/2009 | Hegeman et al. | |
| 7,635,838 B2 | 12/2009 | Herron | |
| 7,668,293 B2 | 2/2010 | Wraight et al. | |
| 7,728,971 B2 | 6/2010 | Christian et al. | |
| 7,748,265 B2 | 7/2010 | Reid et al. | |
| 7,752,906 B2 | 7/2010 | Pop et al. | |
| 7,775,276 B2 | 8/2010 | Pelletier et al. | |
| 7,817,781 B2 | 10/2010 | Wraight et al. | |
| 2007/0246649 A1 | 10/2007 | Jacobi et al. | |
| 2009/0139768 A1 * | 6/2009 | Castillo | 175/50 |
| 2010/0124313 A1 | 5/2010 | Fujisawa | |
| 2010/0236776 A1 | 9/2010 | Spross et al. | |
| 2011/0040494 A1 * | 2/2011 | Foster | 702/25 |

OTHER PUBLICATIONS

Kelliher, et al. "Performance of a Borehole X-Ray Fluorescence Spectrometer for Planetary Exploration". NASA Langley Research Center. 2008, 8 pages.

* cited by examiner

US 9,708,907 B2

APPARATUS AND METHOD FOR ESTIMATING FORMATION LITHOLOGY USING X-RAY FLOURESCENCE

CROSS REFERENCE TO RELATED APPLICATIONS

This application claims the benefit of an earlier filing date from U.S. Provisional Application Ser. No. 61/479,213 filed Apr. 26, 2011, the entire disclosure of which is incorporated herein by reference.

BACKGROUND

X-ray fluorescence spectroscopy is utilized in the field of subterranean hydrocarbon exploration and production, specifically for providing information regarding properties of a geologic formation, such as lithology and mineralogy, and density information. Such information is useful in determining the types of rocks and minerals present in a formation in order to, for example, assess the presence and quality of hydrocarbon reservoirs and predict the effect of rock-fluid interactions for use in developing completion strategies.

Typical logging tools for X-ray fluorescence utilize one or more X-ray sources that are provided for emitting X-ray radiation through a borehole and into a formation. Signals detected from the formation are affected from X-ray fluorescence resulting from interaction between source emitted or primary X-rays and materials in the tool and in the surrounding borehole. Such signals require additional analysis to account for such undesired fluorescence, and/or tools need to be engineered to reduce or minimize interference from the tool and borehole fluids. Other considerations that are generally taken into account when designing such logging tools include the ability of the tools to adequately penetrate the formation, and to provide a measurement signal having a resolution sufficient to provide desired lithographic information.

SUMMARY

An apparatus for estimating properties of an earth formation includes: a carrier configured to be disposed in a borehole in the earth formation; a sample retriever configured to remove a sample of the earth formation, the sample including solid components of the earth formation; an analysis assembly including a chamber disposed with the carrier and configured to hold the sample, an X-ray source configured to irradiate the sample with X-ray radiation while the sample is disposed in the chamber, and one or more X-ray detectors configured to detect radiation emitted from the sample in response to irradiation from the X-ray source.

A method of estimating properties of an earth formation includes: disposing an X-ray spectroscopy tool in a borehole in the earth formation; removing a sample of the earth formation, the sample including solid components of the earth formation; irradiating the sample with X-ray radiation while the sample is disposed in the tool, and detecting radiation emitted from the sample in response to the irradiation; receiving a measurement spectrum of the radiation emitted from the sample; identifying one or more peaks in the measurement spectrum and estimating a concentration of one or more elements based on the one or more peaks; selecting one or more elemental spectra from a stored library, each elemental spectrum corresponding to a spectral contribution of each estimated element; and comparing each of the one or more elemental spectra to the measurement spectrum and adjusting the estimated concentration of the one or more elements based on the comparison.

DETAILED DESCRIPTION

The subject matter which is regarded as the invention is particularly pointed out and distinctly claimed in the claims at the conclusion of the specification. The foregoing and other features and advantages of the invention are apparent from the following detailed description taken in conjunction with the accompanying drawings in which:

DETAILED DESCRIPTION

Apparatuses and methods for estimating properties of subterranean formations are described herein. The apparatuses and methods provide for sampling of solid formation material and performing in situ x-ray fluorescence spectroscopy of formation samples. A method includes disposing a tool in a borehole, retrieving a sample of a formation including solid formation materials such as rock and mineral materials (which may also include other materials including pore fluids such as water, oil and other fluids), irradiating the sample within the tool with X-ray radiation from a primary X-ray source, qualitatively and quantitatively analyzing the resulting X-ray spectroscopy data and modifying the qualitative and/or quantitative data using a library of elemental spectra to estimate concentrations of elemental constituents of the sample. The elemental spectra may be selected and/or generated based on initially estimated elemental concentrations derived from the qualitative analysis. In one embodiment, the elemental models are generated from mathematical models of the sample, such as Monte Carlo based models or other algorithms. Measurements of various properties of the formation may be taken based on the estimated elemental constituents. Examples of such properties include borehole conditions, oil and gas production quality (e.g. sourness, $H_2S$ concentration), borehole fluid salinity based on Chlorine concentration, mud composition (e.g., Barium), and mineralogical information (e.g., identifying concentrations of constituent elements such as Fe, Ca, Si, Mg and others).

Figure 1:
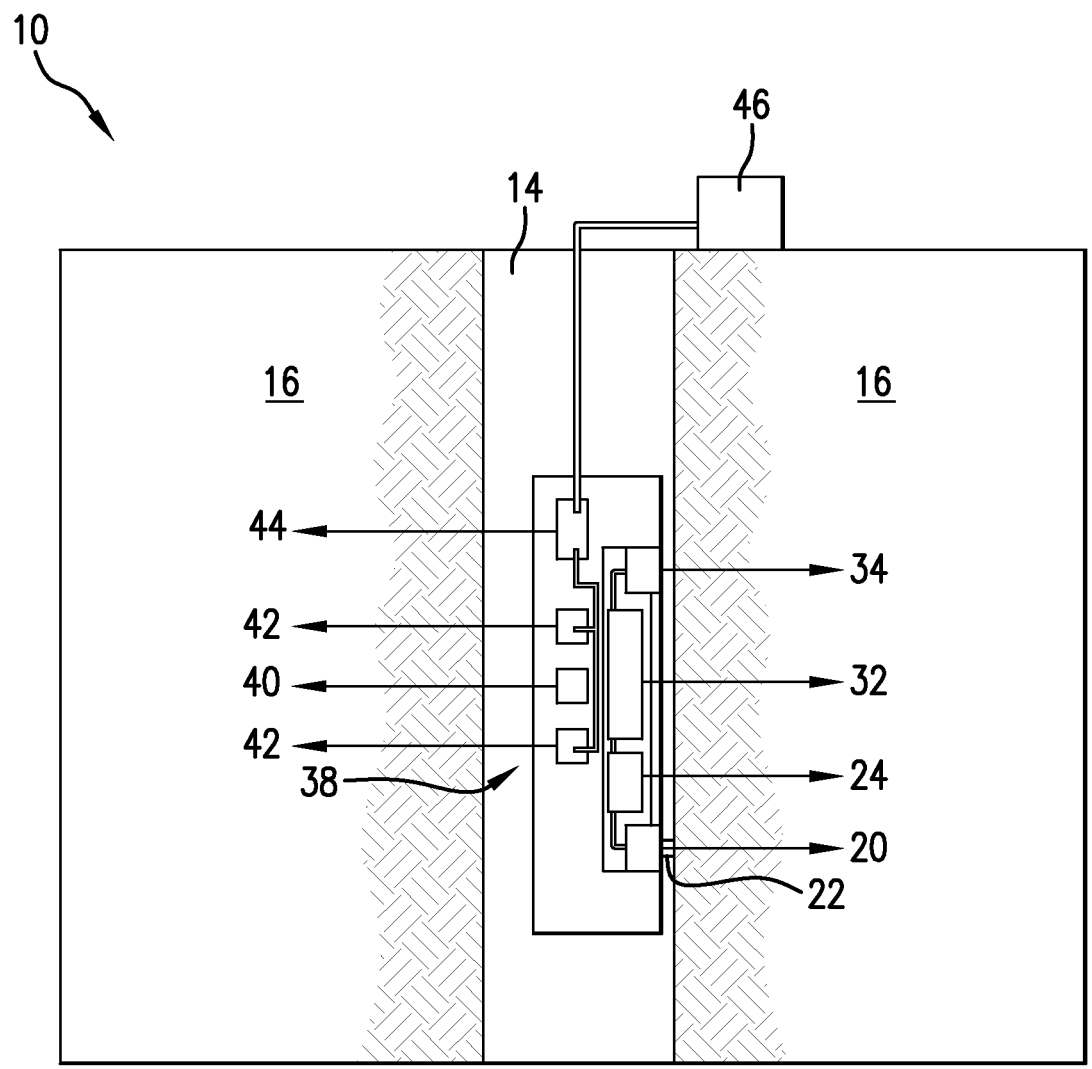
FIG. 1 is a side cross-sectional view of an embodiment of a subterranean x-ray fluorescence spectroscopy system and apparatus.
Figure 2:
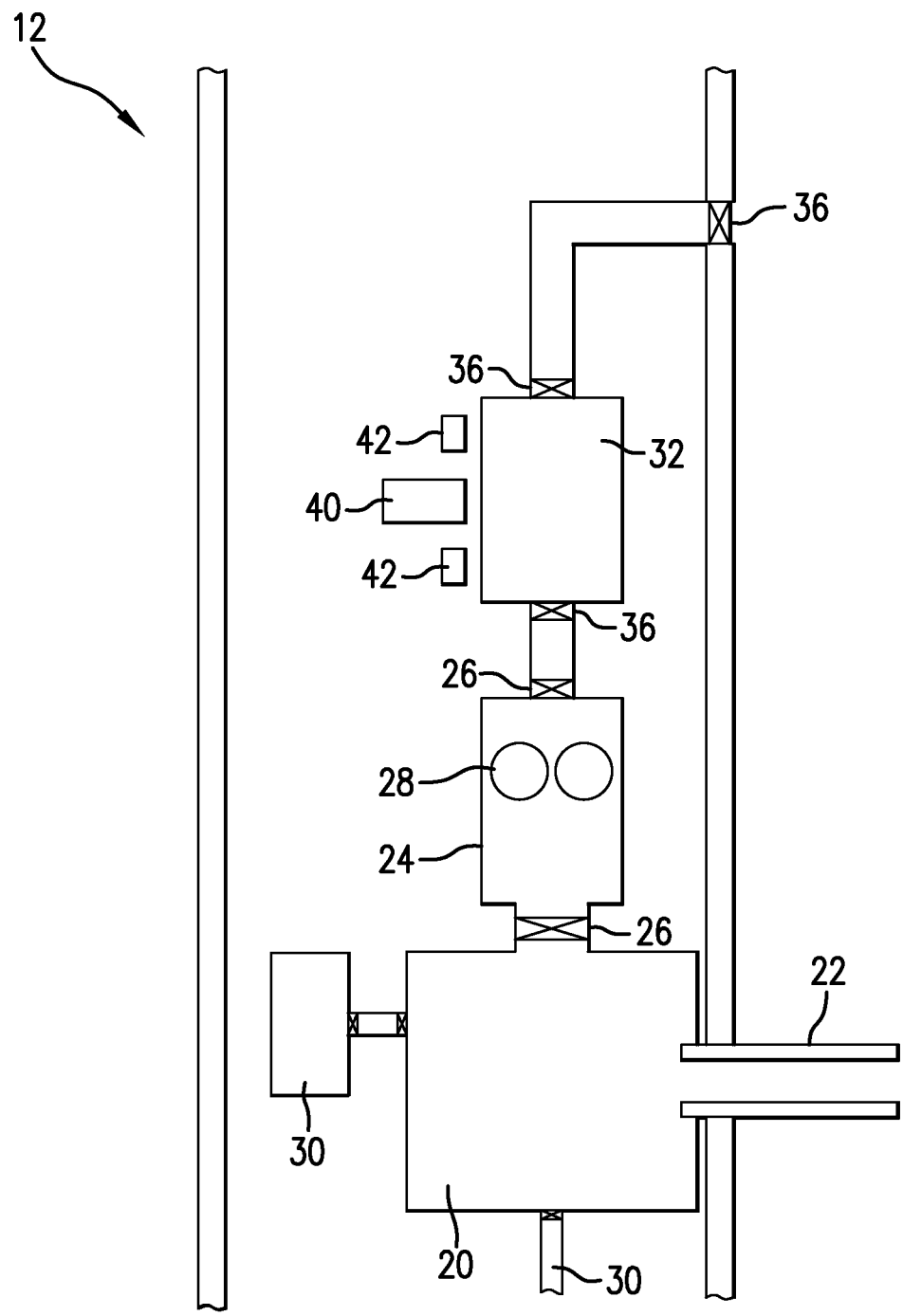
FIG. 2 is a side cross-sectional view of an embodiment of an X-ray spectroscopy tool of the system of FIG. 1.

Referring to FIGS. 1 and 2, an exemplary embodiment of a subterranean borehole and/or formation measurement system 10 includes a downhole tool 12 that is shown disposed in a borehole 14 that penetrates at least one earth formation 16 during a subterranean operation. The borehole 14 may be an open hole or a cased borehole. In one embodiment, the downhole tool 12 is a wireline tool, but is not limited thereto. For example, the downhole tool 12 can be incorporated with a borehole string such as a drill string for logging-while-drilling (LWD) applications. The downhole tool 12 is not limited to the embodiments described herein, and may be disposed with any suitable carrier. A "carrier" as described herein means any device, device component, combination of devices, media and/or member that may be used to convey, house, support or otherwise facilitate the use of another device, device component, combination of devices, media and/or member. Exemplary non-limiting carriers include borehole strings of the coiled tube type, of the jointed pipe type and any combination or portion thereof. Other carrier examples include casing pipes, wirelines, wireline sondes, slickline sondes, drop shots, downhole subs, bottom-hole assemblies, and drill strings.

The downhole tool 12 includes a housing 18 such as a sonde that houses numerous components for retrieving and measuring borehole samples. A sample retriever 20 is configured to remove a sample of the borehole including solid materials such as rock and minerals. The sample may also include additional materials such as water, air, gas and hydrocarbons located, for example, in pores in the solid material. In one embodiment, the sample retriever 20 includes a sample retrieving component such as a coring bit 22 that can be extended through a sidewall of the borehole 14 and retracted to move a sample into the housing 18. In normal operation, sample retrieving component can be stored in the tool 12 for convenience of transporting the tool 12 along the borehole. When a sampling operation commences, the tool 12 can be pushed against the borehole wall and/or the sample retrieving component can be pushed out from the tool to acquire rock samples by, for example, rotary drilling or percussion. The sample retriever may include components such as a pistons and/or hydraulic pumps to move the core sample into the tool 12 and/or advance the core sample through the tool 12.

In one embodiment, the sample retriever is operably connected via a conduit to a sample processing unit such as a grinding and/or mixing unit 24. Such processing may include grinding the rock sample into a granular form (e.g., powder) and mixing the sample via a mixer to stir and stimulate the samples to allow one or more sample volumes to be analyzed. The grinding/mixing unit and/or the sample retriever 20 may include one or more valves 26 so that the sample can be moved into the grinding/mixing unit 24 and retained therein. A mill or other grinding tool 28 is disposed in the grind/mixing unit 24. In one embodiment, the tool 12 includes fluid chambers and/or flow lines 30 in fluid communication with the grinding/mixing unit 24 and/or the sample retriever for the introduction of fluids such as water or solvents, which may be utilized to mix with the sample and/or hydraulically advance the sample through the tool 12. The fluid may be retained with the sample or discarded into the borehole 14 or another chamber.

A sample conveyor 32 is connected via a conduit to the grinding/mixing unit 24 and receives the processed sample. The processed sample(s) are conveyed along inside the sample conveyor 32 and pass through an X-ray analysis region for analysis. The processed samples may then be ejected into the borehole 14 and/or the formation 16 by a sample ejector 34. For example, the sample can be mixed with water or other fluids, or be an a sufficiently fluid state after grinding, and the sample can be pumped through the sample conveyor 32. In other examples, the sample is conveyed via a mechanical system such as a piston assembly. Various valves 36 may be included to control the advancement of the sample through the sample conveyor 32 and ejector 34. Although the sample conveyor 32 is shown as disposed uphole relative to the sample retriever 30 and the grinding and/or mixing unit 24, the configuration is not so limited. For example, the sample retriever 20 may be located uphole relative to the sample conveyor 32 and the unit 24, which can allow for the tool 12 to utilize gravity in conveying the sample therethrough.

An X-ray spectroscopy assembly is included within the housing 18 and/or the tool 12, and includes at least one x-ray source 40 (e.g., an X-ray tube), and one or more X-ray detectors 42. The X-ray source 40 is positioned proximate to the sample conveyor 32 and is positioned to direct X-rays into one or more chambers in the sample conveyor 32. The X-ray detectors 42 are positioned proximate to the sample conveyor 32 to detect radiation emitted from the sample as a result of X-ray fluorescence. An example of a suitable spectroscopy assembly includes an energy dispersive X-ray fluorescence (EDXRF) spectrometer. Although the X-ray assembly is shown as being positioned to irradiate the sample within the sample conveyor 32, the X-ray assembly may be positioned to irradiate the sample in any selected chamber within the tool, such as a chamber within the grinding/mixing unit 24.

The X-ray source 40 includes an X-ray source tube and associated electronics for emitting X-ray particles (photons) to excite the elements of the processed samples. The excited elements, in response to the source radiation, emit secondary characteristic X-Ray particles whose energy and intensity are characteristic and unique to each element in the sample. The X-ray detectors 42 (such as photodiodes) and associated electronics are configured to acquire the secondary characteristic signals excited by elements in the samples, which can be used to generate a pulse height spectrum characterized by all elements in the samples. Any number of detectors may be utilized (e.g., limited by space allowed within the tool 12), as additional detectors can improve detection efficiency. An example of an X-ray detector 42 is a thermoelectrically cooled Si-PIN photodiode X-ray detector.

A processing unit 44 is electrically connected to the X-ray detectors 42 and may also be electrically connected to the X-ray source 40. The processing unit 44 includes suitable processors, memory devices, I/O units and other electronics to receive and process signals from the X-ray detectors 42 and may also be configured to control the X-ray source 40. An example of the processing unit 44 is a Field-Programmable Gate Array (FPGA) computer. The processing unit 44 may include a telemetry unit or otherwise be configured to transmit messages and data to a surface processing unit 46. In one embodiment, the processing unit 44 is configured to send real-time processed X-ray detection and sample analysis results to the surface processing unit 46. The surface processing unit 46 is configured to receive data from the downhole processing unit 44 and/or send electronic directions to operate the downhole X-ray fluorescence assembly.

Figure 3:
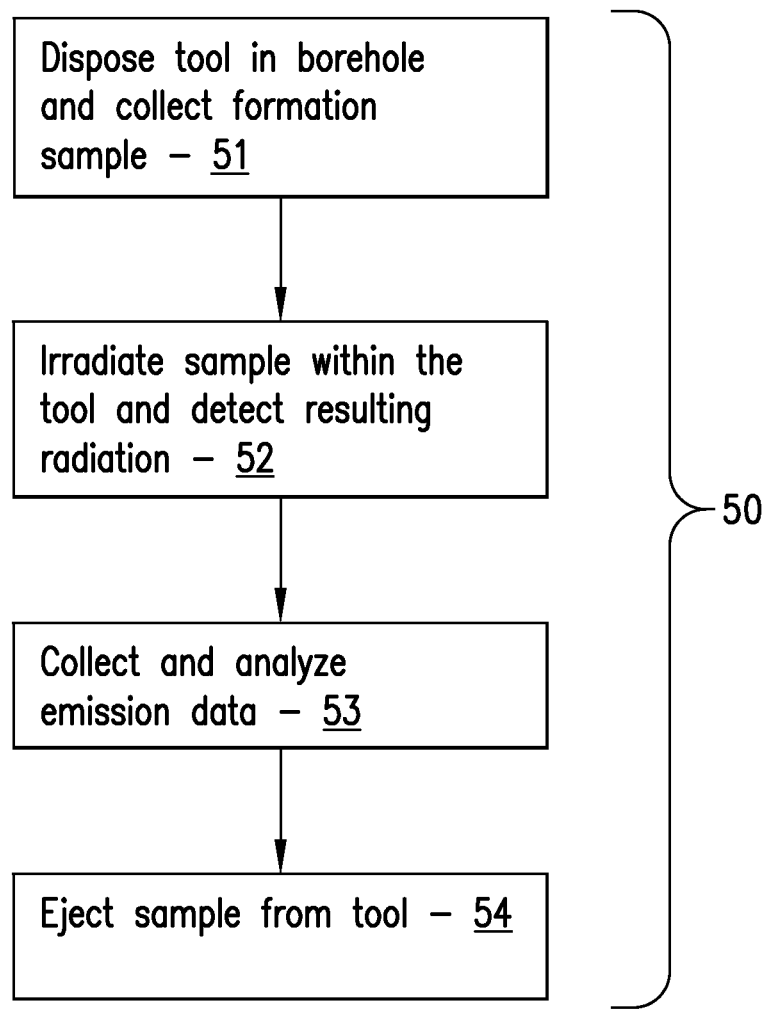
FIG. 3 is a flow chart providing an exemplary method of estimating one or more properties of an earth formation, such as a lithology and mineralogy.
Figure 4:
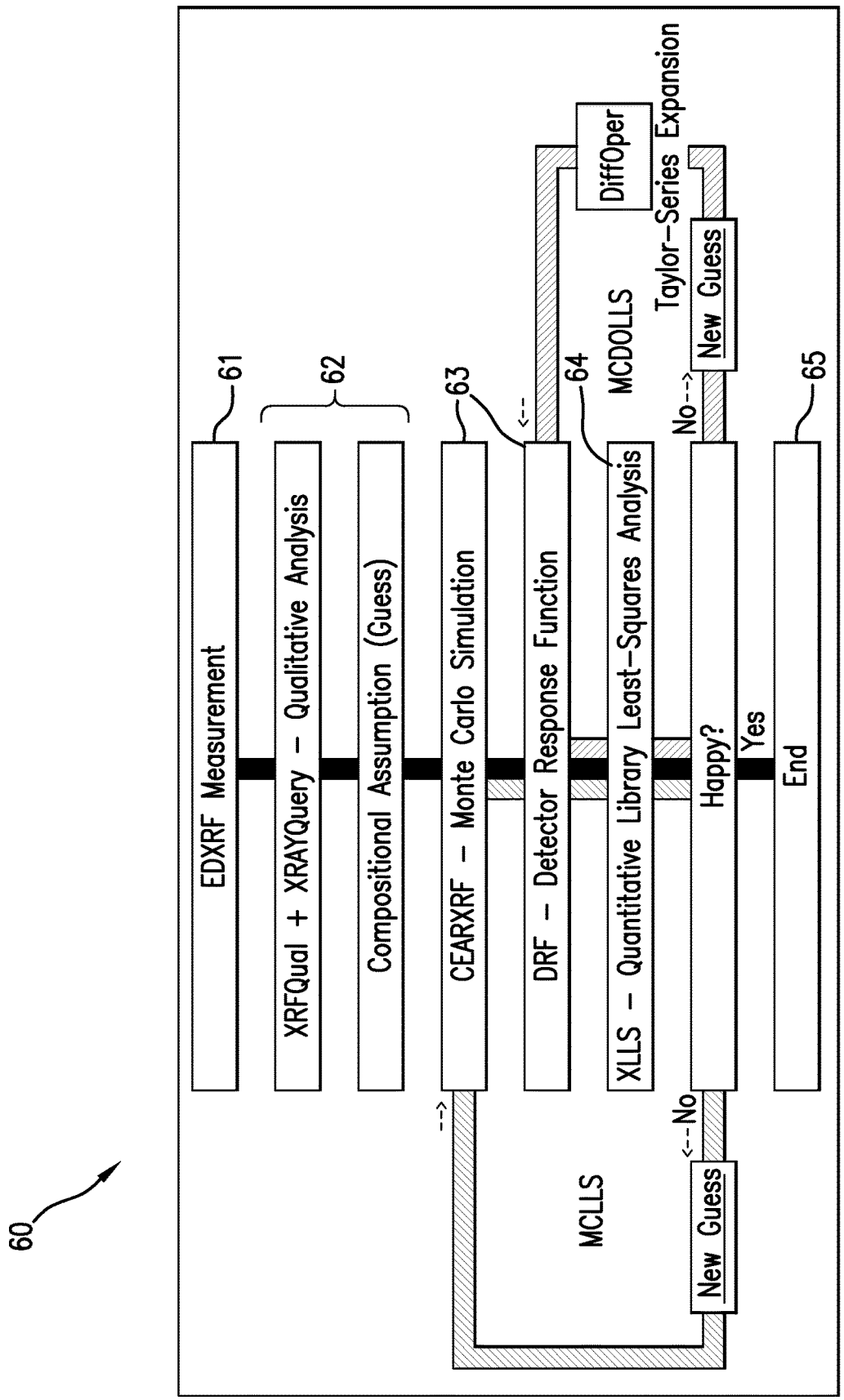
FIG. 4 is a flow chart providing an exemplary method of analyzing X-ray emission data to estimate elemental constituents of an earth formation.

FIG. 3 illustrates a method 50 of estimating properties of an earth formation, including a lithology and mineralogy of the formation. The method 50 may be performed in conjunction with the system 10 and/or the downhole tool 12, but is not limited thereto. The method 50 may be used in conjunction with any apparatus or configuration capable of downhole or subsurface X-ray spectroscopy. The method 50 includes one or more stages 51-54. In one embodiment, the method 50 includes the execution of all of the stages 51-54 in the order described. However, certain stages may be omitted, stages may be added, or the order of the stages changed.

In the first stage 51, the downhole tool 12 is disposed in the borehole 14, and one or more formation samples are taken. In one embodiment, a core sample of the formation, which includes solid (e.g., rock and mineral) materials as well as fluids and/or gases, is taken into the tool 12 via the sample retriever 20. The sample may be ground and/or mixed with desired fluids (e.g., liquids and/or gases) via, for example, the grinding/mixing unit 24.

In the second stage 52, the sample is retained within the tool 12 and one or more X-ray measurements are taken. The X-ray measurements are taken by irradiating the sample with X-ray interrogation signals via an X-ray source such as the X-ray source 40, and detecting resulting X-ray emissions from the sample via one or more detectors such as the X-ray detectors 42.

In the third stage 53, X-ray emission data is collected from the detectors and processed to generate at least one X-ray emission spectrum, referred to herein as a measurement spectrum. In one embodiment, the data is collected and analyzed via the downhole processing unit 44. An exemplary measurement spectrum includes detected photon yields or counts per wavelength or photon energy.

In the fourth stage 54, after the X-ray emission data is collected, the sample is ejected from the tool 12 into the borehole 14 or the formation 16.

FIGS. 4-7 illustrate an embodiment of a method 60 of analyzing X-ray spectroscopy data. The method 60 may be performed in conjunction with the method 50 described above, or may be performed using any received X-ray spectroscopy data. The method 60 includes one or more stages 61-65. In one embodiment, the method 60 includes the execution of all of the stages 61-65 in the order described. However, certain stages may be omitted, stages may be added, or the order of the stages changed. The method may be performed entirely by a processing system, such as the downhole computer, and may be performed and the analysis results transmitted to a user or other location in real-time.

In the first stage 61, an X-ray measurement spectrum, such as an energy dispersive spectrum (e.g., energy dispersive X-ray fluorescence or EDXRF spectrum), is obtained. In one embodiment, the spectrum is obtained via processing of X-ray fluorescence data generated by the downhole tool 12 and the downhole processing unit 44 disposed therein.

Figure 5:
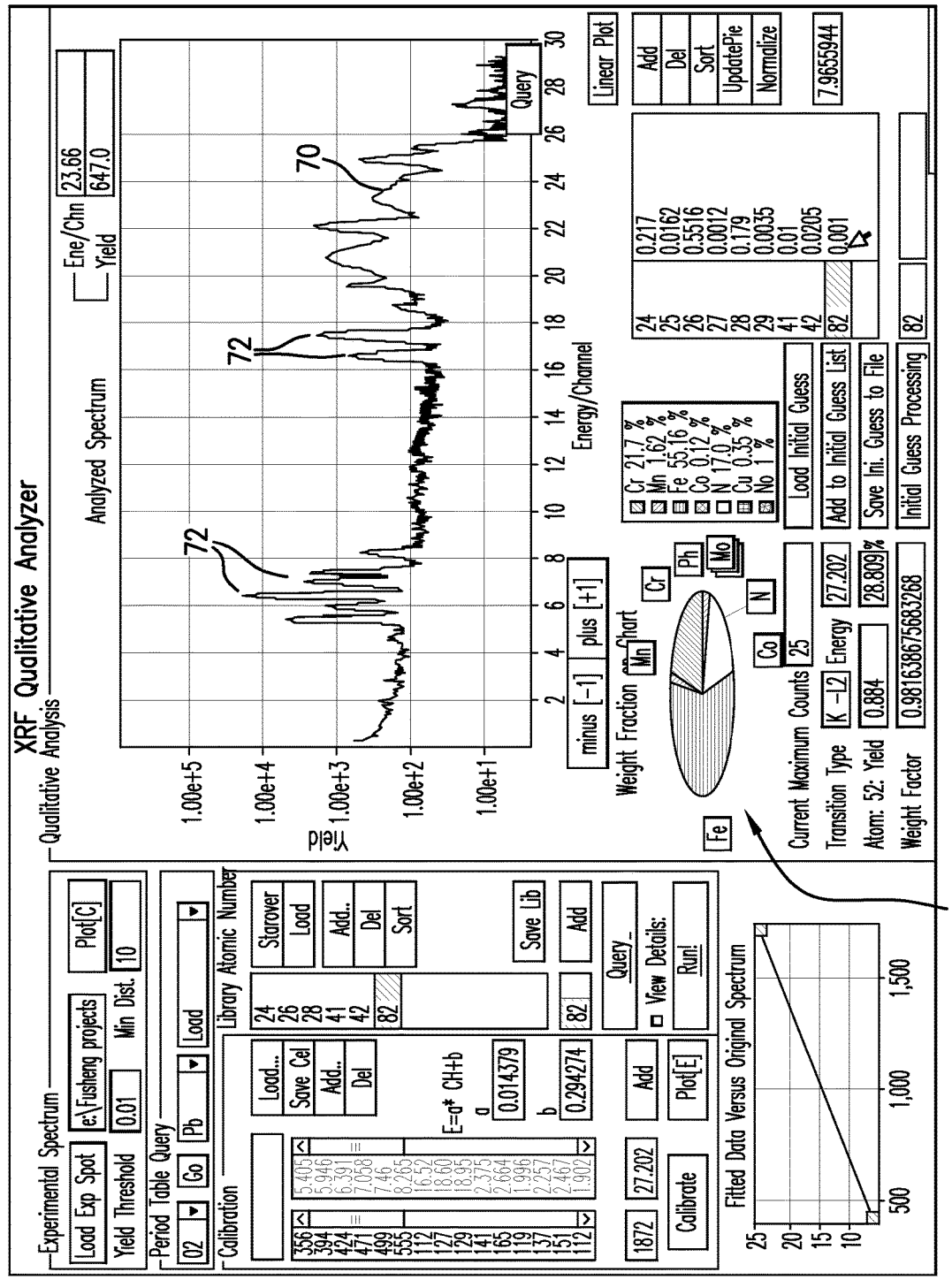
FIG. 5 is an exemplary computer program display showing a measured X-ray fluorescence measurement spectrum and initial estimates of elemental constituents of an earth formation.

In the second stage 62, a qualitative analysis of the measurement spectrum is performed to identify constituent elements and generate initial estimates of each element's concentration (e.g., weight fraction or weight %). This step may be performed automatically by a processing unit such as the processing unit 44 in response to receiving X-ray detector signal data or a measurement spectrum. Qualitative analysis includes identifying various peaks in the measurement spectrum and associating those peaks with constituent elements in the sample. Each element peak may be considered to occur at a known fixed energy or wavelength position and concentrations can be identified by directly relating the concentration of the element with the peak height (e.g., intensity or count rate). The lower limit of the measurement spectrum may depend on the particular measurement instrument's configuration. An example of a measurement spectrum 70 is shown in FIG. 5. The measurement spectrum 70 includes numerous peaks 72 corresponding to X-ray emissions from various elements. The energy associated with the peak, such as peak intensity, is used to generate an initial estimation 74 of the concentration of various elements in the sample. In this example, the initial estimation of the elemental constituents includes Chromium (21.7 weight %), Manganese (1.62 weight %), Iron (55.16 weight %), Cobalt (0.12 weight %), Nitrogen (17.9 weight %), Copper (0.35 weight %), Niobium (1 weight %), and others. Through this step, at least most of the constituent elements having a significant weight percentage can be identified.

This qualitative analysis is coupled with quantitative analysis as described further below. The element concentrations estimated in stage 62 may be affected by various factors which can affect the accuracy of the initial estimations. For example, two or more elements can interact with each other, resulting in contamination and thus skewed results. This effect, called the Matrix Effect, can be overcome by the method described herein. The quantitative analysis is used to adjust the initial estimations, which may be skewed due to such factors.

In the third stage 63, in one embodiment, a mathematical model of the formation sample is generated based on the initial constituent estimates. Various algorithms may be utilized to generate a simulated X-ray emission spectrum of a formation having concentrations of constituent elements according to the initial estimates described above. Other conditions may also be input into the model, such as the type of detector, size and shape of the sample and materials in the sample chamber. In one embodiment, a Monte Carlo model is generated to simulate the X-ray spectral response of a sample having the constituent concentrations initially estimated by the qualitative analysis.

Figure 6:
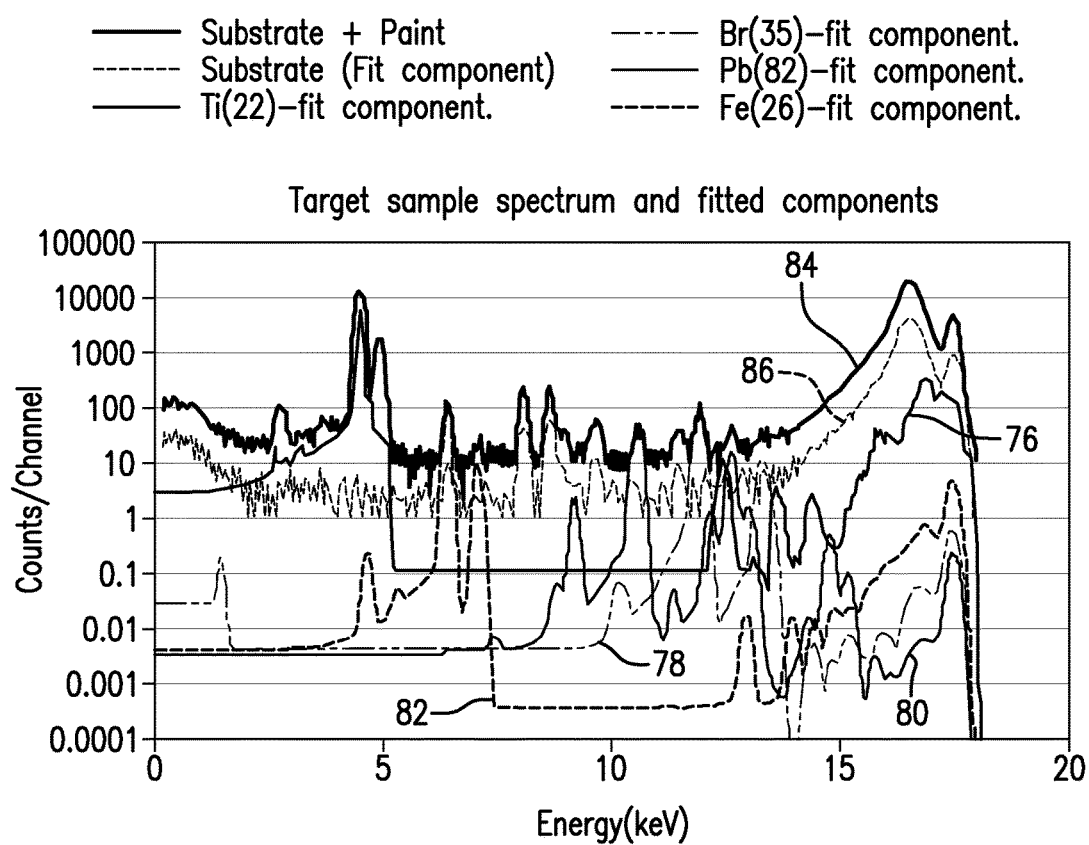
FIG. 6 is an illustration of exemplary elemental spectra corresponding to estimated elemental contributions to an estimated or simulated X-ray fluorescence spectrum.

In one embodiment, a library of stored elemental spectra is generated and/or accessed for elemental concentrations identified in the qualitative analysis, as well as any other elements selected by a user or the processing system. In one embodiment, individual elemental spectra (i.e., a simulated component of a measured or simulated spectrum for a specific element) are produced during the modeling of the sample. Each elemental spectrum provides a contribution to the total spectral response from a respective element. In one embodiment, the elemental spectra are produced during the Monte Carlo modeling process of the simulated spectrum. A detector response function may be applied to the simulated spectrum and elemental spectra to correct for influences on measured spectra due to characteristics of the detector such detector materials and detector chamber sizes. Examples of elemental spectra are shown in FIG. 6. FIG. 6 includes an exemplary library of multiple spectra, although the spectra shown therein do not constitute all of the spectra in this library. Examples of elemental spectra include a Titanium spectrum 76, a Bromine spectrum 78, a Lead spectrum 80 and an Iron spectrum 82. In addition to the elemental spectra, the library may include spectra corresponding to background noise and materials that may affect the X-ray spectroscopy results. Examples include a substrate spectrum 84 detected by the detectors 42 for an empty sample chamber, and a component spectrum 86 corresponding to the spectral contribution of the sample chamber to the total measurement spectrum.

In the fourth stage 64, when the elemental spectra are selected and processed, each elemental spectra is fitted and/or regressed with the measurement spectrum to calculate quantitative estimates of the concentration or weight fraction of each element. In one embodiment, the fitting is a least squares fit. In one embodiment, elements that were not identified during qualitative analysis can be identified here after the first run of the library least squares fit. The quantitative estimates are compared to the initial estimates to determine whether the initial estimates of one or more of the element concentrations should be adjusted.

Figure 7:
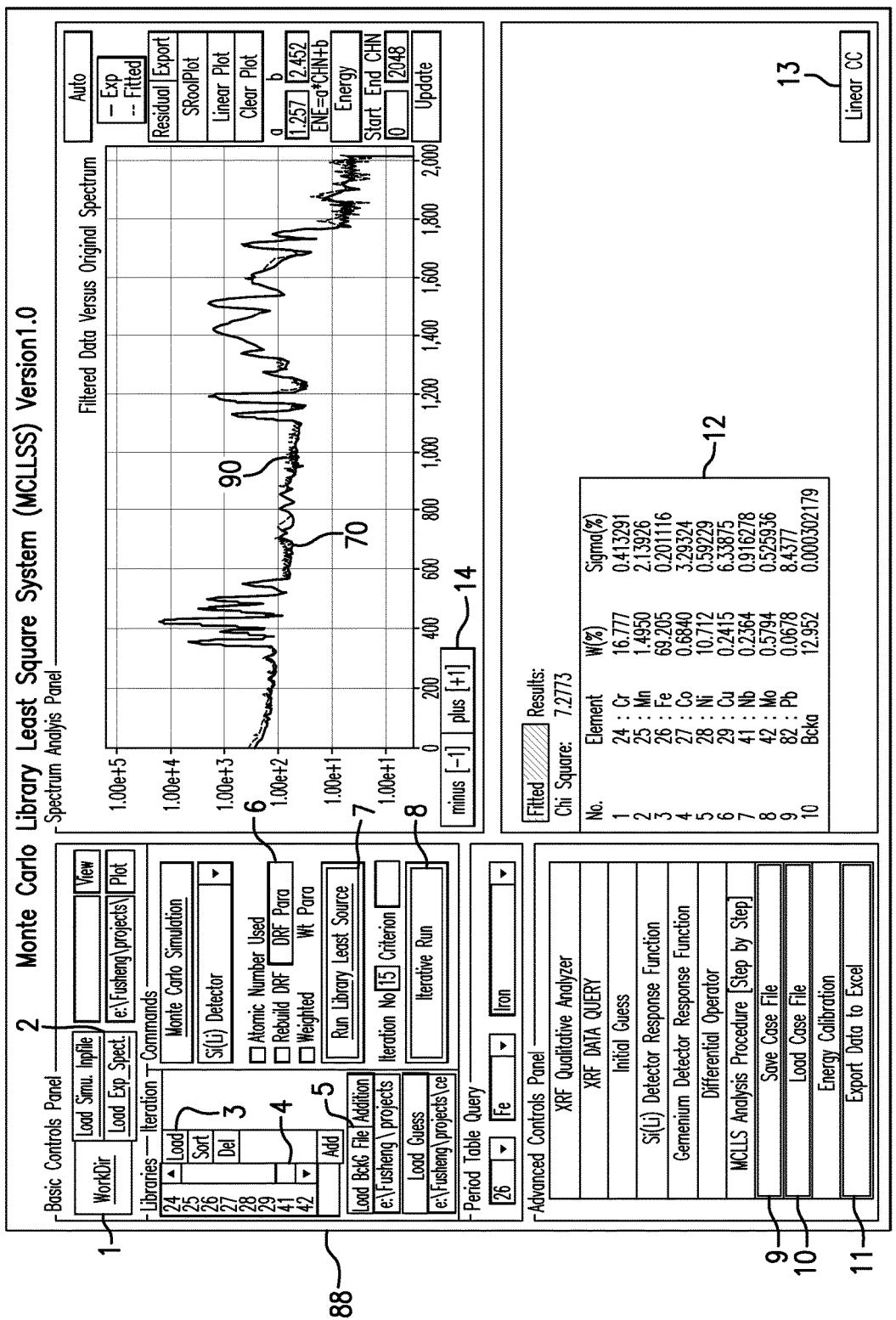
FIG. 7 is an exemplary computer program display showing an exemplary measured X-ray fluorescence spectrum and estimates of elemental constituents of an X-ray fluorescence measurement spectrum derived based on the method of FIG. 4.

For example, as shown in FIG. 7, a library 88 of selected elemental spectra is entered into a processing program. In this example, the elemental spectra are labeled according to their respective atomic numbers. The library is generated which includes each element and its corresponding estimated weight percentage, which was generated from the initial qualitative analysis or from a previous iteration of the method 60. FIG. 7 also illustrates the measurement spectrum 70 and a fitted simulated spectrum 90 generated by stages 63-64. In this example, the simulated spectrum 90 is considered to be an accurate representation of the measurement spectrum 70, and thus the estimated elemental concentrations are considered to be at least sufficiently accurate.

The regression/fit results serve to improve the initial estimates and stages 63-64 may be repeated multiple times to approach satisfactory results. For example, if the quantitatively estimated elemental concentrations for the sample generated in stage 64 are not close enough (e.g., within a selected count range) to those initially estimated for the modeling (e.g., the Monte Carlo calculation), another iteration of stages 63-64 can be performed. In this example, the initial estimated elemental concentrations are adjusted to be closer to that of the measurement spectrum, an adjusted elemental spectrum library is received and/or generated based on the adjusted elemental concentrations, and the adjusted elemental spectra are again fitted to the measurement spectra.

In the fifth stage 65, X-ray fluorescence elemental analysis results from stages 62-64 and measured spectroscopic data may be stored in computer memory within the tool 12. In one embodiment, the results and/or the measured spectroscopic data are sent to a remote and/or surface location such as the surface processing unit 46 as real time information. In one embodiment, the stored spectroscopic data is retained in the tool memory and retrieved when the tool 12 is pulled to the surface for further analysis As described herein, "formations" refer to the various features and materials that may be encountered in a subsurface environment and surround the borehole. Formations include various constituent rocks such as sand, shale, coal, carbonates, and evaporites. The constituents include various minerals such as sandstone, quartz, potassium-feldspar, albite, calcite, dolomite, siderite, anhydrite, illite/smectite, kaolinite, glauconite, chlorite, pyrite, and others. Known elemental compositions derived from the method 50 can be used to identify the rocks, minerals, fluids (e.g., hydrocarbon fluids and gases) and gases present in the sample.

The apparatuses and methods described herein have various advantages over prior art apparatuses and techniques. The apparatuses and methods allow for in-situ retrieval and analysis of formation samples, which provides a more accurate estimation of the constituents of the formation than is achievable with typical prior art techniques that rely on X-ray spectroscopy of formation through a borehole. For example, methods described herein can minimize the effects from a tool body and the borehole since the source, sample, and detectors can be positioned very close to each other inside the tool body and the X-ray source energy can be reduced such that the source X-rays do not penetrate into the tool body and borehole. In addition, the combination analysis using quantitative and qualitative methods described herein also provides an improved estimation of formation constituents.

In connection with the teachings herein, various analyses and/or analytical components may be used, including digital and/or analog systems. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention.

What is claimed is:

1. An apparatus for estimating properties of an earth formation, comprising:
 a carrier configured to be disposed in a borehole in the earth formation;
 a sample retriever configured to remove a sample of the earth formation, the sample including solid components of the earth formation;
 a sample processing unit disposed in the carrier, the sample processing unit configured to process the sample into a fluid state by reducing the solid components to a granular form;
 a sample conveyor configured to advance the processed sample including the granular solid components to an analysis assembly after the sample is processed into the fluid state; and
 the analysis assembly configured to receive the processed sample in the fluid state, the analysis assembly including a chamber disposed with the carrier and configured to hold the processed sample, an X-ray source configured to irradiate the granular solid components with X-ray radiation while the processed sample is disposed in the chamber, and one or more X-ray detectors configured to detect radiation emitted from the processed sample in response to irradiation from the X-ray source.

2. The apparatus of claim 1, wherein the sample processing unit is configured to process the sample by mixing the granular solid components with a liquid.

3. The apparatus of claim 1, wherein the sample processing unit includes a mixing tool configured to stir the granular sample prior to irradiating the granular sample.

4. The apparatus of claim 1, further comprising a processing unit configured to be disposed in the borehole with the carrier and communicably connected to the one or more X-ray detectors.

5. The apparatus of claim 4, wherein the processing unit is configured to receive signal data from the one or more X-ray detectors and generate at least one measurement spectrum from the signal data.

6. The apparatus of claim 5, wherein the processing unit is further configured to:
identify one or more peaks in the measurement spectrum and estimate a concentration of one or more elements based on the one or more peaks;
select one or more elemental spectra from a stored library, each of the one or more elemental spectra corresponding to a spectral contribution of each estimated element; and
compare each of the one or more elemental spectra to the measurement spectrum and adjusting the estimated concentration of the one or more elements based on the comparison.

7. The apparatus of claim 6, wherein the processing unit is configured to estimate the concentration of each of the one or more elements by identifying an element based on a location of a corresponding peak and estimating the concentration of the element based on a height of the corresponding peak.

8. The apparatus of claim 6, wherein the processing unit is further configured to calculate a mathematical model of the sample based on the estimated concentrations, and is further configured to calculate each of the one or more elemental spectra from the mathematical model.

9. The apparatus of claim 6, wherein the processing unit is configured to compare each of the one or more elemental spectra by performing a fit of each of the one or more elemental spectra to the measurement spectrum and calculating a concentration of each element corresponding to each elemental spectra based on the fit.

10. The apparatus of claim 8, wherein the mathematical model is a Monte Carlo model, and the processing unit is configured to compare each of the one or more elemental spectra by performing a library least squares fit of each of the one or more elemental spectra to the measurement spectra.

11. The apparatus of claim 6, wherein the processing unit is connected in communication with a surface location and is configured to transmit results of the comparison to the surface location.

12. A method of estimating properties of an earth formation, comprising:
disposing an X-ray spectroscopy tool in a borehole in the earth formation;
removing a sample of the earth formation, the sample including solid components of the earth formation;
processing the sample into a fluid state, wherein processing includes reducing the solid components to a granular form;
advancing the processed sample including the granular solid components to an analysis assembly after the sample is processed into the fluid state;
irradiating the granular solid components with X-ray radiation by the analysis assembly while the processed sample is disposed in the tool and in the fluid state, and detecting radiation emitted from the processed sample in response to the irradiation;
receiving a measurement spectrum of the radiation emitted from the processed sample;
identifying one or more peaks in the measurement spectrum and estimating a concentration of one or more elements based on the one or more peaks;
selecting one or more elemental spectra from a stored library, each elemental spectrum corresponding to a spectral contribution of each estimated element; and
comparing each of the one or more elemental spectra to the measurement spectrum and adjusting the estimated concentration of the one or more elements based on the comparison.

13. The method of claim 12, wherein estimating the concentration of the one or more elements includes identifying an element based on a location of a corresponding peak and estimating a concentration of the element based on a height of the one or more peaks.

14. The method of claim 12, further comprising calculating a mathematical model of the sample based on the estimated concentrations.

15. The method of claim 14, wherein the mathematical model is a Monte Carlo model.

16. The method of claim 14, further comprising calculating each of the one or more elemental spectra from the mathematical model.

17. The method of claim 12, wherein comparing includes performing a fit of each of the one or more elemental spectra to the measurement spectra and calculating a concentration of each element corresponding to each elemental spectra based on the fit.

18. The method of claim 17, wherein the fit is a least squares fit.

19. The method of claim 14, wherein the mathematical model is a Monte Carlo model, and comparing includes performing a least squares fit of each of the elemental spectra to the measurement spectra.

20. The method of claim 12, further comprising transmitting results of the comparison to the surface location in real time.

* * * * *